US006884585B2

(12) United States Patent
Levine et al.

(10) Patent No.: US 6,884,585 B2
(45) Date of Patent: Apr. 26, 2005

(54) INDUCTION OF BETA CELL DIFFERENTIATION IN HUMAN CELLS BY STIMULATION OF THE GLP-1 RECEPTOR

(75) Inventors: Fred Levine, Del Mar, CA (US); Dominique Dufayet, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 230 days.

(21) Appl. No.: 10/160,336

(22) Filed: May 30, 2002

(65) Prior Publication Data

US 2002/0151065 A1 Oct. 17, 2002

Related U.S. Application Data

(63) Continuation of application No. 09/522,376, filed on Mar. 10, 2000, now Pat. No. 6,448,045.

(51) Int. Cl.[7] .............................................. C12Q 1/68
(52) U.S. Cl. ..................... 435/6; 435/7.1; 435/325; 435/366; 435/440; 435/455
(58) Field of Search ............................ 435/6, 7.1, 440, 435/455, 325, 366

(56) References Cited

U.S. PATENT DOCUMENTS

| 5,424,286 A | 6/1995 | Eng |
| 5,545,618 A | 8/1996 | Buckley et al. |
| 5,614,492 A | 3/1997 | Habener |
| 5,670,360 A | 9/1997 | Thorens |
| 5,705,483 A | 1/1998 | Galloway et al. |
| 5,723,333 A | 3/1998 | Levine et al. |
| 5,858,973 A | 1/1999 | Habener et al. |
| 5,977,071 A | 11/1999 | Galloway et al. |
| 5,981,488 A | 11/1999 | Hoffmann |

FOREIGN PATENT DOCUMENTS

| WO | WO 00/09666 A2 | 2/2000 |

OTHER PUBLICATIONS

Gang Xu et al., "Exendin–4 Stimulates Both β–Cell Replication and Neogenesis, Resulting in Increased β–Cell Mass and Improved Glucose Tolerance in Diabetic Rats," Dec. 1999, Diabetes, vol. 48, pp. 2270–2276.

Jie Zhou et al., "Glucagon–Like Peptide 1 and Exendin–4 Convert Pancreatic AR42J Cells Into Glucagon–and Insulin–Producing Cells," Dec. 1999, Diabetes, vol. 48, pp. 2358–2366.

Gillian M. Beattie et al., "Sustained Proliferation of PDX–1[+] Cells Derived From Human Islets," May 1999, Diabetes, vol. 48, pp. 1013–1019.

Tanya L. Halvorsen et al., "Telomerase Activity is Sufficient to Allow Transformed Cells to Escape from Crisis," Mar. 1999, Molecular and Cellular Biology, pp. 1864–1870.

Dufayet, Dominique et al.; β–Cell Differentiation from a Human Pancreatic Cell Line *in Vitro* and *in Vivo*; *Molecular Endocrinology*, 2001, vol. 15, No. 3, pp. 476–483.

Itkin–Ansari, P. et al,; "Introduction of PDX–1 into an adult human pancreatic β–cell line expressing SV40 T–antigen and H–ras–va112", *Experimental and Clinical Endocrinology and Diabetes*, 1997, vol. 105, No. 4, p. A22.

Wang, Xiaolin et al,; "Glucagon–like peptide–1 Regulates the Beta Cell Transcription Factor, PDX–1, in Insulinoma cells"; *Endocrinology*, 1999, vol. 140, No. 10, pp. 4904–4907.

*Primary Examiner*—James Ketter
*Assistant Examiner*—David Lambertson
(74) *Attorney, Agent, or Firm*—Townsend and Townsend and Crew, LLP (57) ABSTRACT

The present invention provides methods for inducing insulin gene expression in cultured pancreas cells, the method comprising contacting a culture of endocrine pancreas cells expressing a PDX-1 gene with a GLP-1 receptor agonist, wherein the cells have been cultured under conditions such that the cells are in contact with other cells in the culture, thereby inducing insulin gene expression in the cells. The invention also provides high throughput screening methods for modulators of β-cell function, stable cultures of cells made by the methods of the invention, and methods of treating a human subject using the methods of the invention.

13 Claims, 6 Drawing Sheets

INDUCTION OF BETA CELL DIFFERENTIATION IN HUMAN CELLS BY STIMULATION OF THE GLP-1 RECEPTOR

STATEMENT AS TO RIGHTS TO INVENTIONS MADE UNDER FEDERALLY SPONSORED RESEARCH AND DEVELOPMENT

This invention was made with Government support under Grant No. 5 R01 DKK55283-02 and 5 R01 DK55065-02, awarded by the National Institutes of Health. The Government has certain rights in this invention.

CROSS-REFERENCES TO RELATED APPLICATIONS

Not applicable.

BACKGROUND OF THE INVENTION

Transplantation of cells exhibiting glucose-responsive insulin secretion has the potential to cure diabetes. However, this approach is limited by an inadequate supply of cells with that property, with is exhibited only by pancreatic β-cells. The development of expanded populations of human β-cells that can be used for cell transplantation is therefore a major goal of diabetes research (D. R. W. Group, "Conquering diabetes: a strategic plan for the 21st century" *NIH Publication No.* 99-4398 (National Institutes of Health, 1999)). A number of alternative approaches are being pursued to achieve that goal, including using porcine tissue as a xenograft (Groth et al., *J Mol Med* 77:153–4 (1999)), expansion of primary human β-cells with growth factors and extracellular matrix (Beattie et al., *Diabetes* 48:1013–9 (1999)), and generation of immortalized cell lines that exhibit glucose-responsive insulin secretion (Levine, *Diabetes/Metabolism Reviews* 1: 209–46 (1997)).

Although there has been great interest in using porcine islets, they are difficult to manipulate in vitro and concerns have been raised about endogenous and exogenous xenobiotic viruses being transmitted to graft recipients (Weiss, *Nature* 391:327–8 (1998)). With primary human β-cells, entry into the cell cycle can be achieved using hepatocyte growth factor/scatter factor ("HGF/SF") plus extracellular matrix ("ECM") (Beattie et al., *Diabetes* 48:1013–9 (1999), Hayek et al., *Diabetes* 44:1458–1460 (1995)). However, this combination, while resulting in a 2–3×10$^4$-fold expansion in the number of cells, is limited by cellular senescence and loss of differentiated function, particularly pancreatic hormone expression (Beattie et al., *Diabetes* 48:1013–9 (1999)).

Immortalized cell lines from the human endocrine pancreas have been created to develop β-cell lines that exhibit glucose responsive insulin secretion (Wang et al., *Cell Transplantation* 6:59–67 (1997), Wang et al., *Transplantation Proceedings* 29:2219 (1997), Halvorsen et al., *Molecular and Cellular Biology* 19:1864–1870 (1999)). The cell lines are made by infecting primary cultures of cells from various sources including adult islets, fetal islets, and purified β-cells, with viral vectors expressing the potent dominant oncogenes such as SV40 T antigen and H-ras$^{val12}$ (Wang et al., *Cell Transplantation* 6:59–67 (1997), Wang et al., *Transplantation Proceedings* 29:2219 (1997), Halvorsen et al., *Molecular and Cellular Biology* 19:1864–1870 (1999); see also U.S. Pat. No. 5,723,333). The combined effect of those oncogenes is to trigger growth factor-independent and extracellular matrix (ECM)-independent entry into the cell cycle, as well as to prolong the lifespan of the cells from 10–15 population doublings or primary cells to approximately 150 doubling for the oncogene-expressing cells (Halvorsen et al., *Molecular and Cellular Biology* 19:1864–1870 (1999)). Further introduction of the gene encoding the hTRT component of telomerase results in immortalization, allowing the cells to be grown indefinitely (Halvorsen et al., *Molecular and Cellular Biology* 19:1864–1870 (1999)).

Although the cell lines grow indefinitely, they lose differentiated function, similar to growth-stimulated primary β-cells. Methods of stimulating differentiation of the cell lines into insulin-secreting β-cells are therefore desired. Such cells could then be transplanted in vivo as a treatment for diabetes.

SUMMARY OF THE INVENTION

Induction of β-cell differentiation in cultured human β-cells was achieved by stimulating multiple signaling pathways, including those downstream of the homeodomain transcription factor PDX-1, cell-cell contact, and the glucagon-like peptide-1 (GLP-1) receptor. Synergistic activation of those pathways resulted in differentiation of the cultured human β-cells, which initially express no detectable pancreatic hormones, into fully functional β-cells that exhibit glucose-responsive insulin secretion. Furthermore, these cells can be transplanted in vivo and demonstrate glucose-responsive expression of insulin. The ability to grow unlimited quantities of functional human β-cells in vitro provides the means for a definitive cell transplantation therapy for treatment of diabetes.

In one aspect, the present invention provides a method for inducing insulin gene expression in cultured endocrine pancreas cells, the method comprising the steps of (i) expressing a PDX-1 gene in cells that have been cultured under conditions such that the cells are in contact with other cells in the culture; and (ii) contacting the cells with a GLP-1 receptor agonist, thereby inducing insulin gene expression in the cells.

In another aspect, the present invention provides a method of identifying a compound that modulates β-cell function, the method comprising the steps of contacting cells made by the method described above with the compound and determining the effect of the compound on β-cell function.

In another aspect, the present invention provides a stable culture of endocrine pancreas cells, wherein the cells are in contact with other cells in the culture, wherein the cells express a PDX-1 gene, and wherein insulin gene expression is stimulated in the cells when exposed to an effective amount of a GLP-1 receptor agonist.

In another aspect, the present invention provides a method of treating a diabetic subject by providing to the subject cells that secrete insulin in response to glucose, the method comprising the steps of: (i) contacting a culture of endocrine pancreas cells expressing a PDX gene with a GLP-1 receptor agonist, wherein the cells have been cultured under conditions such that the cells are in contact with other cells in the culture; and (ii) administering the cells to the subject, thereby providing to the subject cells that secrete insulin in response to glucose.

In one embodiment, the GLP-1 receptor agonist is a GLP-1 analog or has an amino acid sequence of a naturally occurring peptide. In another embodiment, the GLP-1 receptor agonist is GLP-1, exendin-3, or exendin-4.

In one embodiment, the cells are cultured as aggregates in suspension.

In one embodiment, the PDX-1 gene is endogenous to the cells. In another embodiment, the PDX-1 gene is recombinant.

In one embodiment, the cells are human cells. In another embodiment, the cells are βlox5 cells. A deposit of the βlox5 cells, which are human pancreatic cells, was made on Jul. 19, 2001 under accession number PTA-3532 at the American Type Culture Collection, 10801 University Boulevard, Manassas, Va. 20110-2209.

In one embodiment, the cells express a recombinant oncogene. In another embodiment, the cells express a recombinant oncogene. In another embodiment, the cells express a recombinant oncogene. In another embodiment, the cells express a recombinant telomerase gene.

In one embodiment, the diabetic subject is a human. In another embodiment, the subject has Type I insulin dependent diabetes.

BRIEF DESCRIPTION OF THE DRAWINGS

FIG. 2(A) insulin;

FIG. 2(B) quantitative RT-PCR analysis of insulin gene expression;

FIG. 2(C) other pancreatic hormones. Aggregation of cells into three-dimensional clusters and the retroviral vector expressing PDX-1 have been described previously (Itkin-Ansari et al., submitted). Exendin-4 (Sigma) was used at a concentration of 10 nM. RT-PCR for insulin, somatostatin, glucagon, and IAPP have been described previously (Itkin-Ansari et al., submitted). Quantitative RT-PCR was done by interpolation from a standard curve constructed using a plasmid containing the human insulin cDNA.

FIG. 3(A) electrophoretic mobility shift assay (EMSA) of PDX-1. EMSA for PDX-1 was performed using a probe derived from the human insulin promoter A5 element.

FIGS. 3(B&C) RT-PCR analysis of BETA2 and Pax6.

FIG. 3(D) Western blot analysis of CREB.

FIG. 3(E) EMSA of RIPE3b.

FIG. 4(A–C) Insulin immunohistochemistry;

FIG. 4(D) Insulin western blot analysis of conditioned medium.

FIG. 5(A) RT-PCR for glucokinase.

FIG. 5(B) Radioimmunoassay for insulin secreted from induced βlox5 cells grown in culture medium containing increasing concentrations of glucose. Induced βlox5 cells were cultured in DME containing a single concentration of added glucose for one hour. Medium was harvested and assayed for insulin by RIA.

DETAILED DESCRIPTION OF THE INVENTION

Introduction

Beginning with a cell line that exhibited few β-cell characteristics, despite having been originally derived from human β-cells, complete β-cell function has been successfully induced in vitro. In addition, thee cells have been transplanted into mice and are shown to produce insulin in a glucose responsive manner. Induction of β-cell differentiation in cells such as βlox5 cells requires three inducing factors, PDX-1, cell-cell contact, and GLP-1 receptor agonists such as exendin-4. Cultured cell lines such as TRM-6 (δ-cell lineage) and βlox5 (β-cell lineage) are powerful tools that should allow identification of the full complement of genes that are required for endocrine cell development and function. Furthermore, the requirement for multiple interacting inducing factors provides an opportunity to study how different signal transduction pathways interact with one another to control a complex differentiation program.

The availability of an unlimited source of functional human β-cells has important implications for diabetes. One straightforward application is in exploring aspects of β-cell biology that would benefit from an unlimited, homogeneous source of cells. High-throughput screening for new diabetes drugs is one such application. The cells of the invention can be used, e.g., to screen for small molecule or macromolecule GLP-1 receptor agonists or other compounds that enhance insulin expression. In addition, cells such as those described herein can be used in a cell transplantation therapy for diabetes. Cells that express PDX-1 and are in cell-to-cell contact with other cells are stimulated with a GLP-1 receptor agonist, as described herein. Such cells are then transplanted into a suitable mammalian host, preferably a human. Such cells exhibit glucose-responsive insulin secretion in vivo.

In one embodiment, cultured cells useful in the practice of the invention express one or more oncogenes, such as SV40 T antigen and Hras$^{val12}$, which minimally transform the cells but stimulate growth and bypass cellular senescence. Other suitable oncogenes include, e.g., HPV E7, HPV E6, c-myc, and CDK4 (see also U.S. Pat. No. 5,723,333). In addition, the cells can be transduced with an oncogene encoding mammalian telomerase, such as hTRT, to facilitate immortalization. Suitable oncogenes can be identified by those of skill in the art, and partial lists of oncogenes are provided in Bishop et al., *RNA Tumor Viruses*, vol. 1, pp. 1004–1005 (Weiss et al., eds, 1984), and Watson et al., *Molecular Biology of the Gene* (4$^{th}$ ed. 1987). In some cases the oncogenes provide growth factor-independent and ECM-independent entry into the cell cycle. Often the oncogenes are dominant oncogenes. The cells can be analyzed for recombinant oncogene expression by analysis of oncogene RNA or protein expression. Integration of an oncogene into the genome can be confirmed, e.g., by Southern blot analysis. Often, the oncogenes are delivered to the cells using a viral vector, preferably a retroviral vector, although any suitable expression vector can be used to transduce the cells (see, e.g., U.S. Pat. No. 5,723,333, which describes construction of vectors encoding one or more oncogenes and transduction of pancreas endocrine cells, see also Halvorsen et al., *Molecular and Cellular Biology* 19:1864–1870 (1999)).

The vector used to create the cell lines incorporates recombinase sites, such as lox sites, so that the oncogenes can be deleted by expression of a recombinase, such as the cre recombinase, in the cells following expansion (Halvorsen et al., *Molecular and Cellular Biology* 19:1864–1870 (1999)). Deletion of the oncogenes is useful for cells that are to be transplanted in to a mammalian subject. Other recombinase systems include *Saccharomyces cerevisiae* FLP/FRT, lambda att/Int, R recombinase of *Zygosaccharomyces rouxii*. In addition, transposable elements and transposases could be used. Deletion of the oncogene can be confirmed, e.g., by analysis of oncogene RNA or protein expression, or by Southern blot analysis.

The cultured cells of the invention also express either endogenous or recombinant PDX-1 having PDX-1 activity, e.g., alleles, polymorphic variants, and orthologs (see, e.g., Sander et al., *J. Mol Med.* 71:327–340 (1997)). Endogenous expression of PDX-1 can be induced using transcription factors such as hepatocyte nuclear factor 3 beta, which is involved in pancreatic β-cell expression of the PDX-1 gene (see, e.g., Wu et al., *Molecular and Cellular Biology* 17:6002–6013 (1997)). Recombinant PDX-1 is delivered to the cells using expression vectors, e.g., viral vectors such as retroviral vectors, as described above.

The vectors used to transduce the cells can by any suitable vector, including viral vectors such as retroviral vectors. Preferably, the vector is one that provides stable transformation of the cells, as opposed to transient transformation.

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

GLP-1 receptor agonists, which are administered to the cells of the invention, include naturally occurring peptides such as GLP-1, exendin-3, and exendin-4 (see, e.g., U.S. Pat. No. 5,424,286; U.S. Pat. No. 5,705,483, U.S. Pat. No. 5,977,071; U.S. Pat. No. 5,670,360; U.S. Pat. No. 5,614,492), GLP-1 analogs (see, e.g., U.S. Pat. No. 5,545,618 and U.S. Pat. No. 5,981,488), and small molecule analogs. GLP-1 receptor agonists may be tested for activity as described in U.S. Pat. No. 5,981,488. Cells are contacted with a GLP-1 receptor agonist in a time and amount effective to induce insulin mRNA expression, as described herein. Typically, the cells are contacted with the GLP-1 receptor agonists for a discrete time period, as the GLP-1 receptor agonist is believed to act as a switch for insulin gene expression. Continuous administration of the GLP-1 receptor agonist is therefore not required.

Immune rejection of grafted cells has previously been a major obstacle to successful islet transplantation. Any universal human donor cell will be recognized by the immune system as an allograft. However, recent advances in therapy for allograft rejection may make this less of a concern (see, e.g., Kenyon et al., *Proc. Natl Acad. Sci. USA* 96:8132–7 (1999)). An advantage of using an immortalized cell line as a source of transplantable cells is that they can be engineered to exhibit desirable qualities, including avoidance or suppression of host immune responses.

Cell Culture

This invention relies upon routine techniques in the field of cell culture, and suitable methods can be determined by those of skill in the art using known methodology (see, e.g., Freshney et al., *Culture of Animal Cells* ($3^{rd}$ ed. 1994)). In general, the cell culture environment includes consideration of such factors as the substrate for cell growth, cell density and cell contract, the gas phase, the medium, and temperature.

The cells of the invention are grown under conditions that provide for cell to cell contact. In a preferred embodiment, the cells are grown in suspension as three dimensional aggregates. Suspension cultures can be achieved by using, e.g., a flask with a magnetic stirrer or a large surface area paddle, or on a plate that has been coated to prevent the cells from adhering to the bottom of the dish. In a preferred embodiment, the cells are grown in Costar dishes that have been coated with a hydrogel to prevent them from adhering to the bottom of the dish.

For the cells of the invention that are cultured under adherent conditions, plastic dishes, flasks, roller bottles, or microcarriers in suspension are used. Other artificial substrates can be used such as glass and metals. The substrate is often treated by etching, or by coating with substances such as collagen, chondronectin, fibronectin, and laminin. The type of culture vessel depends on the culture conditions, e.g., multi-well plates, petri dishes, tissue culture tubes, flasks, roller bottles, and the like.

Cells are grown at optimal densities that are determined empirically based on the cell type. For example, a typical cell density for βlox5 cultures varies from $1 \times 10^3$ to $1 \times 10^7$ cells per ml. Cells are passaged when the cell density is above optimal.

Cultured cells are normally grown in an incubator that provides a suitable temperature, e.g., the body temperature of the animal from which is the cells were obtained, accounting for regional variations in temperature. Generally, 37° C. is the preferred temperature for cell culture. Most incubators are humidified to approximately atmospheric conditions.

Important constituents of the gas phase are oxygen and carbon dioxide. Typically, atmospheric oxygen tensions are used for cell cultures. Culture vessels are usually vented into the incubator atmosphere to allow gas exchange by using gas permeable caps or by preventing sealing of the culture vessels. Carbon dioxide plays a role in pH stabilization, along with buffer in the cell media and is typically present at a concentration of 1–10% in the incubator. The preferred $CO_2$ concentration typically is 5%.

Defined cell media are available as packaged, premixed powders or presterilized solutions. Examples of commonly used media include DME, RPMI 1640, DMEM, Iscove's complete media, or McCoy's Medium (see, e.g., GibcoBRL/ Life Technologies Catalogue and Reference Guide; Sigma Catalogue). Typically, low glucose DME or RPMI 1640 are used in the methods of the invention. Defined cell culture media are often supplemented with 5–20% serum, typically heat inactivated, e.g., human horse, calf, and fetal bovine serum. Typically, 10% fetal bovine serum is used in the methods of the invention. The culture medium is usually buffered to maintain the cells at a pH preferably from 7.2–7.4. Other supplements to the media include, e.g., antibiotics, amino acids, sugars, and growth factors such as hepatocyte growth factor/scatter factor.

Pharmaceutical Compositions and Administration

Pharmaceutically acceptable carriers are determined in part by the particular composition being administered (e.g., cell), as well as by the particular method used to administer the composition. Accordingly, there are a wide variety of suitable formulations of pharmaceutical compositions of the present invention (see, e.g., *Remington's Pharmaceutical Sciences*, $17^{th}$ ed., 1989).

Formulations suitable for parenteral administration, such as, for example, by intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by direct surgical transplantation under the kidney, intraportal administration, intravenous infusion, or intraperitoneal infusion.

Injection solutions and suspensions can be prepared from sterile powders, granules, and tablets. The dose administered to a patient, in the context of the present invention should be sufficient to effect a beneficial therapeutic response in the patient over time. The dose will be determined by the efficacy of the particular cells employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the cells to be administered in the treatment or prophylaxis of conditions owing to diminished or aberrant insulin expression, the physician evaluates cell toxicities, transplantation reactions, progression of the disease, and the production of anti-cell antibodies. For administration, cells of the present invention can be administered in amount effective to provide normalized glucose responsive-insulin production and normalized glucose levels to the subject, taking into account the side-effects of the cell type at various concentrations, as applied to the mass and overall health of the patient. Administration can be accomplished via single or divided doses.

Assays for Modulators of B-Cell Function

A. Assays

Assays using the cultured cells of the invention can be used to test for inhibitors and activators of β-cell function, e.g., insulin production and/or glucose responsive insulin production. Such modulators are useful for treating various disorders involving glucose metabolism, such as diabetes and hypoglycemia. Treatment of dysfunctions include, e.g., diabetes mellitus (all types); hyperinsulinism caused by insulinoma, drug-related, e.g., sulfonylureas or excessive insulin, immune disease with insulin or insulin receptor antibodies, etc. (see, e.g., Harrison's Internal Medicine (14th ed. 1998)).

Modulation is tested using the cultures of the invention by measuring insulin gene expression, optionally with administration of glucose, e.g., analysis of insulin mRNA expression using northern blot, dot blot, PCR, oligonucleotide arrays, and the like; and analysis of insulin protein expression (preproinsulin, proinsulin, insulin, or c-peptide) using, e.g., western blots, radio immune assays, ELISAs, and the like. Downstream effects of insulin modulation can also be examined. Physical or chemical changes can be measured to determine the functional effect of the compound on β cell function. Samples or assays that are treated with a potential inhibitor or activator are compared to control samples without the test compound, to examine the extent of modulation.

B. Modulators

The compounds tested as modulators of β-cell function can be any small chemical compound, or a macromolecule, such as a protein, sugar, nucleic acid or lipid. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487–493 (1991) and Houghton et al., Nature 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909–6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217–9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309–314 (1996) and PCT/US96/10287), carbohydrate libraries (see, e.g., Liang et al., Science, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

The assays can be solid phase or solution phase assays. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100- about 1500 different compounds. It is possible to assay many plates per day; assay screens for up to about 6,000, 20,000, 50,000, or 100,000 or more different compounds is possible using the integrated systems of the invention.

Definitions

As used herein, the following terms have the meanings ascribed to them unless specified otherwise.

"Inducing insulin gene expression" refers to increasing, in a cell or culture of cells, the level of expression from the insulin gene by at least about 25%, preferably 50%, 100%, 500%, 1000%, 5000%, or higher, as compared to a negative control culture. Insulin gene expression can be measured by methods known to those of skill in the art, e.g., by measuring insulin RNA expression, preproinsulin, proinsulin, insulin, or c-peptide production, e.g., using PCR, hybridization, and immunoassays.

Cells that "secrete insulin in response to glucose" are cells or a cell culture that, in comparison to a negative control (either non-insulin responsive cells or insulin responsive cells that are not exposed to glucose), have increased insulin secretion in response to glucose of at least about 25%, preferably 50%, 100%, 500%, 1000%, 5000%, or higher than the control cells (measured as described above).

"Culturing cells" so that the cells are "in contact with other cells in the culture" refers to culture conditions that allow cell to cell contact. Under such conditions, many but not all cells are in contact with one or more other cells of the culture. Such conditions include culturing the cells on a solid surface, such as a plate or a bead, or culturing the cells in suspension.

"Endocrine pancreas cells" refers to cells originally derived from an adult or fetal pancreas, preferably islet cells. "Cultured" endocrine pancreas cells refers to primary cultures as well as cells that have been transformed with genes such as an oncogene, e.g., SV40 T antigen, ras, or a telomerase gene (e.g., hTRT).

A "GLP-1 receptor agonist" refers to GLP-1, a GLP-1 analog, or a naturally occurring peptide that binds to the GLP-1 receptor (e.g., exendin-3 or -4), thereby activating signal transduction from the receptor.

"Culturing" refers to growing cells ex vivo or in vitro. Cultured cells can be non-naturally occurring cells, e.g., cells that have been transduced with an exogenous gene such as an oncogene or a transcription factor such as PDX-1. Cultured cells can also be naturally occurring isolates or primary cultures.

A "stable" cell line or culture is one that can grow in vitro for an extended period of time, such as for at least about 50 cell divisions, or for about 6 months, more preferably for at least about 150 cell divisions, or at least about ten months, and more preferably at least about a year.

"Modulating β-cell function" refers to a compound that increases (activates) or decreases (inhibits) glucose responsive insulin secretion of an endocrine pancreas cell. Glucose responsive insulin secretion can be measured by a number of methods, including analysis of insulin mRNA expression, preproinsulin production, proinsulin production, insulin production, and c-peptide production, using standard methods known to of skill in the art. To examine the extent of modulation, cultured cells are treated with a potential activator or inhibitor and are compared to control samples without the activator or inhibitor. Control samples (untreated with inhibitors or activators) are assigned a relative insulin value of 100%. Inhibition is achieved when the insulin value relative to the control is about 90%, preferably 75%, 50%, and more preferably 25–0%. Activation is achieved when the insulin value relative to the control is 110%, more preferably 125%, 150%, and most preferably at least 200–500% higher or 1000% or higher.

"Transduction" refers to any method of delivering an exogenous nucleic acid, e.g., an expression vector, to a cell, including transfection, lipofection, electroporation, viral transduction, microinjection, particle bombardment, receptor mediated endocytosis, and the like.

A diabetic subject is a mammalian subject, often a human subject, that has any type of diabetes, including primary and secondary diabetes, type 1 NIDDM-transient, type 1 IDDM, type 2 IDDM-transient, type 2 NIDDM, and type 2 MODY, as described in *Harrison's Internal Medicine,* 14th ed. 1998.

"Expressing" a gene refers to expression of a recombinant or endogenous gene, e.g., resulting in mRNA or protein production from the gene. A recombinant gene can be integrated into the genome or in an extrachromosomal element.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$–$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

The term "immunoassay" is an assay that uses an antibody to specifically bind an antigen, e.g., ELISA, western blot, RIA, immunoprecipitation and the like. The immunoassay is characterized by the use of specific binding properties of a particular antibody to isolate, target, and/or quantify the antigen.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

In one embodiment of the invention the expression vector is a viral vector, preferably one that integrates into the host cell genome, such as a retroviral vector, or an adeno-associated viral vector. Examples of retroviruses, from which viral vectors of the invention can be derived, include avian retroviruses such as avian erythroblastosis virus (AMV), avian leukosis virus (ALV), avian mycloblastosis virus (ABV), avian sarcoma virus (ACV), spleen necrosis virus (SNV), and Rous sarcoma virus (RSV); non-avian retroviruses such as bovine leukemia virus (BLV); feline retroviruses such as feline leukemia virus (FeLV) or feline sarcoma virus (FeSV); murine retroviruses such as murine leukemia virus (MuLV), mouse mammary tumor virus (MMTV), murine sarcoma virus (MSV), and Moloney murine sarcoma virus (MoMSV); rat sarcoma virus (RaSV); and primate retroviruses such as human T-cell lymphotropic viruses 1 and 2 (HTLV-1, 2) and simian sarcoma virus (SSV). Many other suitable retroviruses are know to those of skill in the art. Often the viruses are replication deficient, i.e., capable of integration into the host genome but not capable of replication to provide infective virus.

In another embodiment of the invention, the vector is a transient vector such as an adenoviral vector, e.g., for transducing the cells with a recombinase to delete the integrated oncogenes.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I

Preparation of Immortalized Human Pancreatic B-Cell Lines

Figure 1:
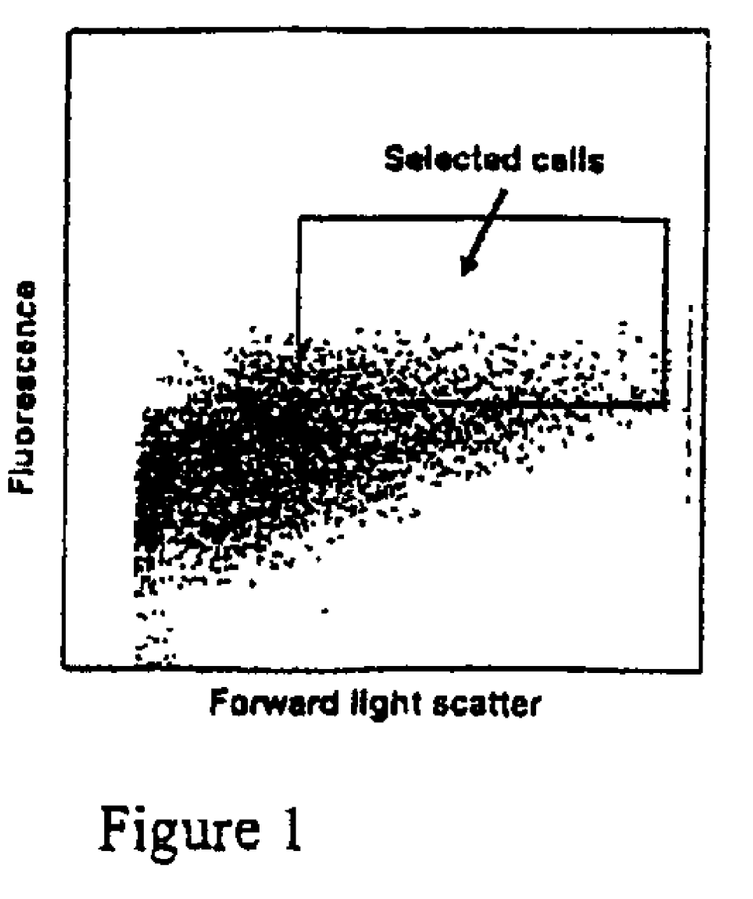
FIG. 1. Flow cytometric analysis of FAD autofluorescence in a single cell suspension of human islets used to develop the βlox5 cell line.

To develop cell lines from human β-cells, islet preparations were enriched for β-cells based on flavin adenine dinucleotide (FAD) autofluorescence prior to retroviral infection, as described below (FIG. 1). Immunohistochemical analysis showed that cells with low FAD autofluorescence contained mostly α with a small number of β cells, while cells with high FAD autofluorescence (selected cells in box) contained 96% insulin-positive cells. Glucagon but not insulin was detectable by RIA in culture medium from the low FAD population, while insulin but not glucagon was detectable in culture medium from high FAD cells.

Figure 2:
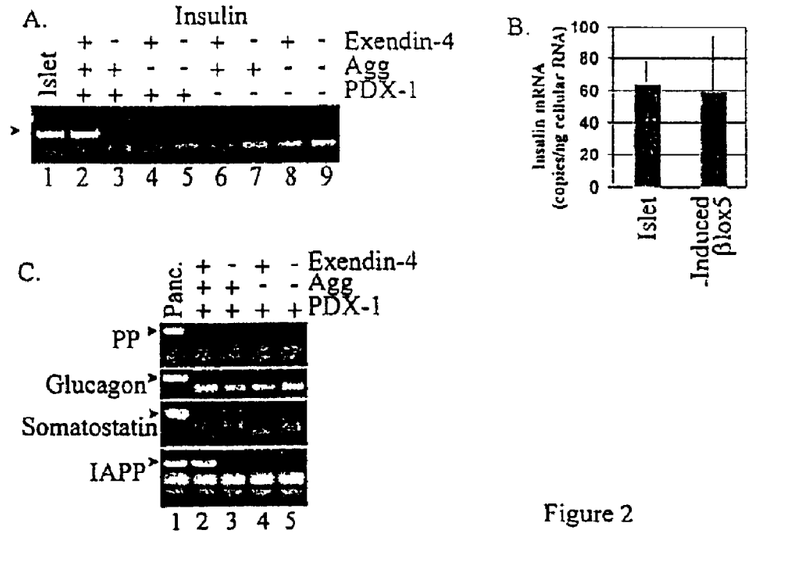
FIG. 2: RT-PCR analysis of pancreatic hormone gene expression in βlox5. The conditions tested were βlox5 cells grown in monolayer culture, βlox5 cells infected with a retroviral vector expressing PDX-1, βlox5 cells grown as three-dimensional aggregates, and βlox5 cells treated with exendin-4.

The 96% pure insulin-positive population was used to create the βlox5 cell line by infection with the LTPRRNLlox retroviral vector expressing SV40 T antigen and H-ras$^{val12}$ (Halvorsen et al., *Molecular and Cellular Biology* 19:1864–1870 (1999)). This cell line exhibits an extended lifespan and is immortalized by infection with a retroviral vector expressing the hTRT telomerase gene (Halvorsen et al., *Molecular and Cellular Biology* 19:1864–1870 (1999)). Insulin was detectable at low levels shortly after selection in G418, but was rapidly lost (FIG. 2A, lane 9). Furthermore, βlox5 does not express other pancreatic hormones (FIG. 2C).

To isolate the cells, a single cell suspension was prepared from an adult islet preparation of 80% purity. Islets with a diameter of 50–100 μm were handpicked under direct vision using a stereoscope after staining with dethrone (60 μmol/L). Picked islets were incubated overnight in RPMI containing 2.5 mM glucose, then dissociated into single cells using non-enzymatic dissociating solution (Sigma Corp., St Louis, Mo.) and shaking in a 37° C. water bath at 60 cycles/minute as previously described. The resulting single cell suspension was analyzed in a fluorescence-activated cell sorter (Facstar Plus, Becton Dickinson, Mansfield Mass.) and particle flavin adenine dinucleotide (FAD) autofluorescence (510–550 nm) was plotted against forward light scatter. Two islet cell populations became apparent when FAD autofluorescence (510–550 nm) was plotted against forward light scatter, as previously described for rat islets.

Highly autofluorescing cells were sorted into sterile Hanks BSS, washed and resuspended in RPMI containing 5 mM glucose and 10% FBS at a concentration of 2×10$^6$ cells/ml. Cells were aggregated into cell clusters by placing 50 μl droplets in a petri dish, gently inverting, and incubating overnight. Thereafter monolayers were initiated from the cell aggregates as previously described for adult islets on HTB-9 matrix in the presence of HGF/SF. After 2–3 days, when the cells were observed to be dividing, they were infected with high titer retroviral vector.

Example II

Growth Factor Expression in βlox5 Cells

Figure 3:
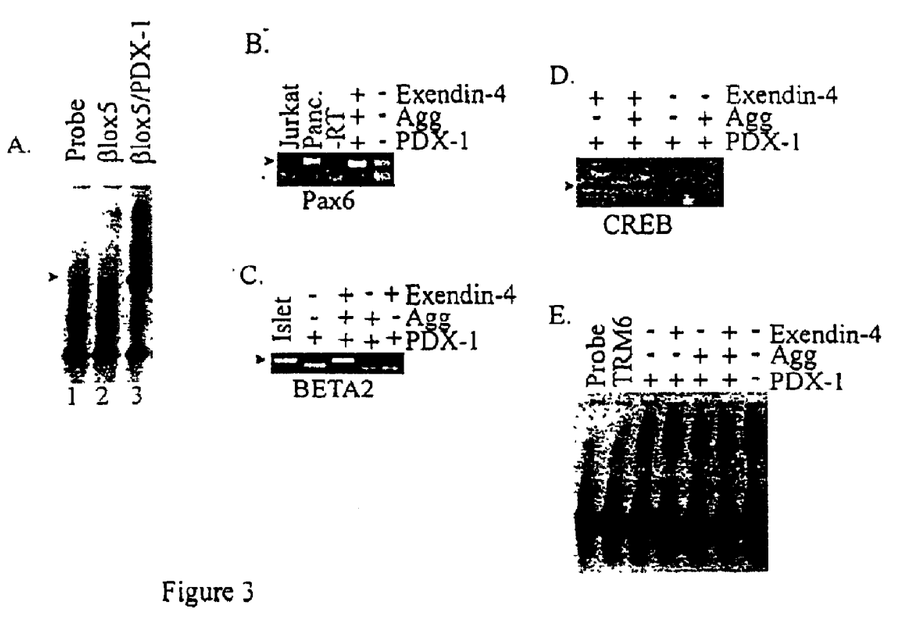
FIG. 3: Analysis of transcription factors expressed in βlox5 cells.

The expression of some of the transcription factors that are important in establishing and maintaining β-cell differentiated function was examined (FIG. 3). Most significantly, PDX-1, a homeodomain transcription factor that is required for β-cell development and function, is not expressed in βlox5, as shown by RT-PCR (not shown) or EMSA (FIG. 3A, lane 2). This result differs from growth-stimulated primary cells, where PDX-1 continues to be expressed (Beattie et al., *Diabetes* 48:1013–9 (1999)). BETA2, a bHLH factor important in neurogenesis as well as β-cells is not expressed in βlox5. CREB, which plays a critical role in cAMP responsiveness in β-cells, is also not expressed (FIG. 3D). However, Pax6, which is expressed in all endocrine cells, was expressed at high levels in βlox5, consistent with an origin from primary endocrine cells. RIPE3b, a factor that binds to an element in the insulin promoter but that has not yet been isolated, is present as detected by EMSA (not shown). Overall, some, but not all, of the transcription factors that play important roles in establishing and maintaining β-cell function are expressed in βlox5 cells.

Example III

Expression of Recombinant PDX-1 in βlox5 Cells

Previously, it has been shown that introduction of PDX-1 into a cell line, TRM-6, derived from human fetal islets, resulted in an increase in somatostatin gene expression. PDX-1 also acted synergistically with cell-cell contact to further increase the level of somatostatin expression about 1,000-fold above the cells not expressing PDX-1, to a level similar to that found in normal human islets. To determine whether βlox5 could be induced to express pancreatic hormones, recombinant PDX-1 was expressed in βlox5 using a retroviral vector. While this resulted in functional PDX-1 expression in the cells (FIG. 3A, lane 3), in contrast to TRM-6, βlox5 did not respond to PDX-1 and cell-cell contact with an increase in hormone expression (FIG. 2A, lane 3, FIG. 2C, lane 3), despite the fact that PDX-1 expression in βlox5 resulted in functional protein as evidenced by its ability to bind DNA in EMSA (FIG. 3A, lane 3). Therefore, other factors were examined for their ability to induce hormone expression in βlox5 cells expressing PDX-1. Activin and betacellulin have been reported to be able to induce endocrine differentiation in cell lines and primary cells (Mashima et al., *Diabetes* 48:304–9 (1999), Huotari et al., *Endocrinology* 139, 1494–9 (1998), Mashima et al., *J Clin Invest* 97:1647–54 (1996), Yamaoka et al., *J Clin Invest* 102:294–301 (1998)). However, they had no effect on hormone expression in βlox5 cells (data not shown).

Example III

Treatment of PDX-1 Expressing Cells with GLP-1

GLP-1, a small peptide cleaved from the proglucagon molecule, is an insulin secretogogue Drucker et al., *Diabetes* 47:159–69 (1998)). A homolog of GLP-1 derived from Gila lizards, exendin-4, has recently been found to stimulate rodent β-cell differentiation in vitro and in vivo (Xu et al., *Diabetes* 48:2270–2276 (1999), Zhou et al., *Diabetes* 48:2358–66 (1999). Therefore, exendin-4 was tested for its ability to stimulate β-cell differentiation in βlox5. 10 nmolar exendin-4 was administered to the cells for four days, and then removed from the culture medium.

By itself, exendin-4 had no effect on hormone expression in βlox5 (FIG. 2A, lane 8). However, when βlox5 cells expressing PDX-1 were grown in suspension culture as three-dimensional aggregates in the presence of the exendin-4, a substantial amount of insulin mRNA was detectable (FIG. 2A, lane 2). The nature of the interaction between exendin-4, cell-cell contact, and PDX-1 is evident from the fact that no hormone mRNA was detectable with any one or two of the three inducing factors (FIG. 2A). Quantitative RT-PCR revealed that the level of insulin mRNA in induced βlox5 cells was as that found in adult islets (FIG. 2B). Islet amyloid polypeptide (IAPP) mRNA, a hormone that is co-secreted with insulin, was also expressed in induced βlox5 cells (FIG. 2C, lane 2). However, the other major pancreatic hormones, glucagon, somatostatin, and pancreatic polypeptide (PP), were not induced (FIG. 2C).

Example IV

Expression of Pancreatic Hormones in PDX-1 Expressing βlox5 Cells

The expression of transcription factors important in β-cell development was examined to determine whether they had been induced by PDX-1, cell-cell contact, and exendin-4. BETA2 was induced only by the combination of all three inducing factors (FIG. 3C). Interestingly, CREB, which plays an important role in the cAMP response of β-cells, was induced by exendin-4 alone, independently of cell-cell contact and PDX-1 (FIG. 3D). GLP-1 has been reported to increase cAMP levels and this has been thought to be a major mechanism by which GLP-1 acts as an insulin secretogogue (Serre et al., *Endocrinology* 139:4448–54 (1998)). This is the first report that activation of the GLP-1 receptor can induce CREB expression, suggesting that GLP-1 may act at multiple levels in promoting cAMP signaling. RIPE3b, a factor that plays a critical role in insulin gene expression but that has not yet been cloned, is expressed in βlox5 irrespective of PDX-1, cell-cell contact, or exendin-4 (FIG. 3E).

Example V

Glucose Responsiveness

Figure 4:
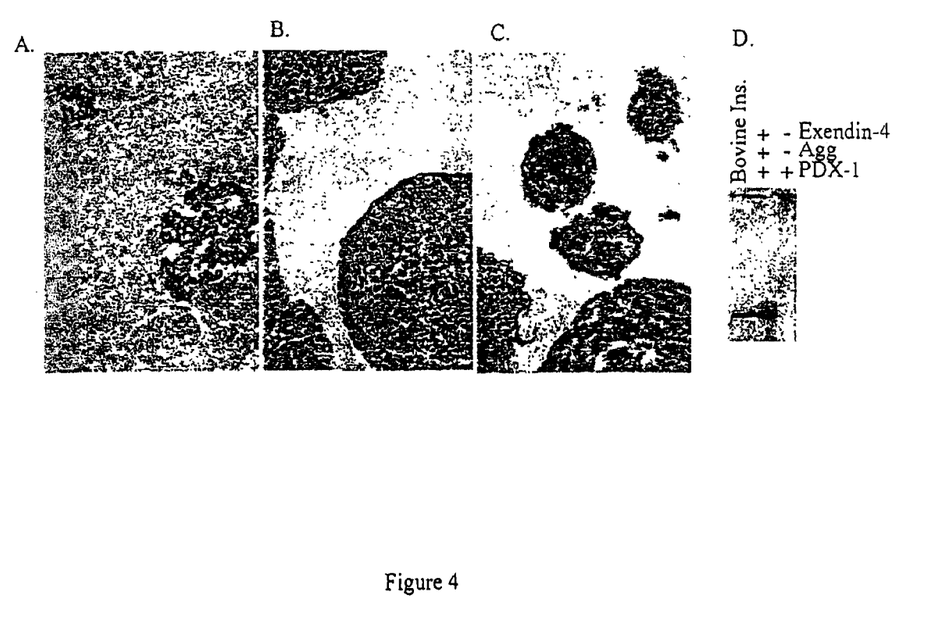
FIG. 4. Insulin protein in induced βlox5 cells.
Figure 5:
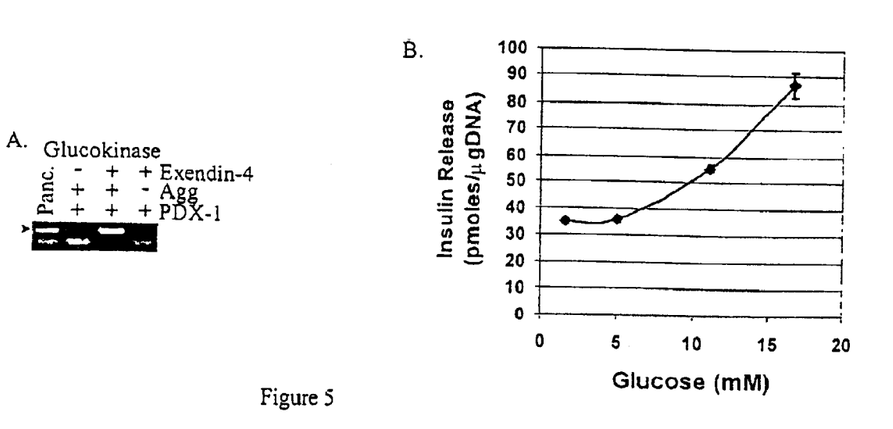
FIG. 5. Analysis of glucose-responsive insulin secretion.

A hallmark of functional β-cells is the ability to secrete insulin in response to blood glucose. Primary β-cells store large quantities of insulin and secrete it in response to a variety of physiological stimuli, most significantly extracellular glucose. Induced βlox5 cells have an insulin content of 6 picograms per microgram DNA at 1.6 mM glucose. Intracellular insulin is easily detectable by immunohistochemistry (FIG. 4A). Media from induced βlox5 cells contains mature insulin that comigrates with bovine insulin (FIG. 4B). A major component of the glucose-sensing apparatus is glucokinase (Matschinsky et al., *Diabetes* 47:307–315 (1998)). Induced βlox5 cells express glucokinase mRNA, while uninduced cells do not (FIG. 5A). The extent to which βlox5 cells exhibit glucose-responsive insulin secretion was tested by culturing βlox5 cells in different concentrations of glucose and measuring insulin release in the culture medium by RIA (FIG. 5B). Half-maximal secretion occurred at approximately 11 mM, similar to normal adult islets.

Example VI

Figure 6:
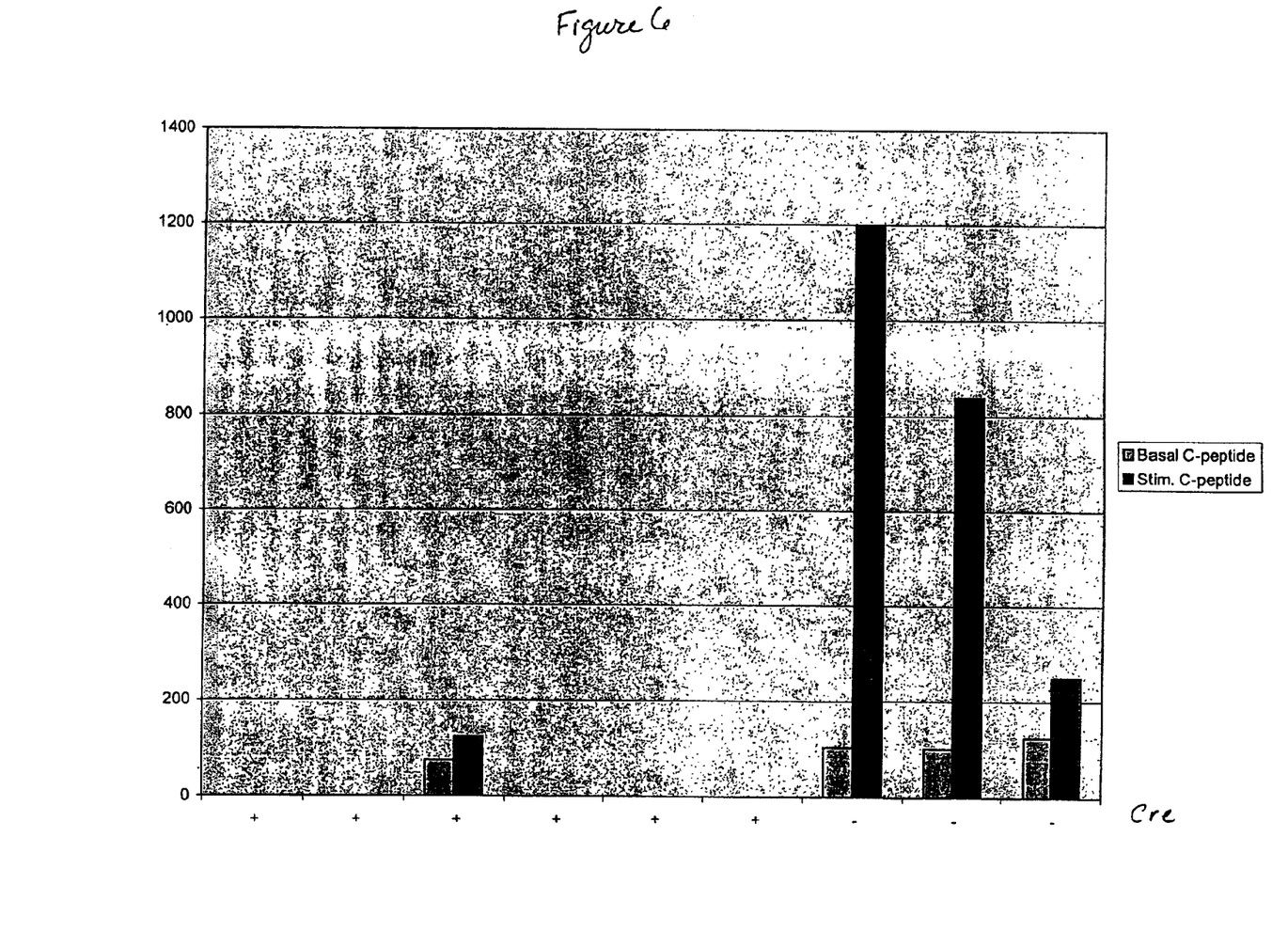
FIG. 6. RIA of c-peptide in nude mice transplanted with induced βlox5 cells.

Transplantation of Glucose Responsive Cells in Vivo

βlox5 cells expressing PDX-1 were transfected with an adenoviral vector expressing cre, to excise the recombinant SV40 T antigen and H-ras$^{val12}$ genes, as described in Halvorsen et al., *Molecular and Cellular Biology* 19:1864–1870 (1999). The cells had been previously stimulated with exendin-4, as described above. The cells were transplanted under the kidney capsule of nude mice for three months. One to ten million cells were transplanted in a mice that weighed about 25 grams. After three months, the mice were bled for c-peptide and the grafts were harvested. C-peptide was measured according to standard procedures using RIA (FIG. 6). These cells exhibit glucose-responsive insulin secretion.

What is claimed is:

1. A method of identifying a compound that modulates β-cell function, the method comprising
   (i) expressing a recombinant polynucleotide encoding PDX-1 in β-cells that have been cultured under conditions such that the cells are in cell-to-cell contact in the culture; and
   (ii) contacting the cells with a GLP-1 receptor agonist, thereby inducing insulin gene expression in the cells;
   (iii) contacting the cells with a test compound; and
   (iv) determining the effect of the test compound on pancreatic cell function to identify a compound that modulates β-cell function.

2. The method of claim 1, wherein the GLP-1 receptor agonist is a GLP-1 analog.

3. The method of claim 1, wherein the GLP-1 receptor agonist has an amino acid sequence of a naturally occurring peptide.

4. The method of claim 1, wherein the GLP-1 receptor agonist is GLP-1, exendin-3, or exendin-4.

5. The method of claim 1, wherein the cells are cultured as aggregates in suspension.

6. The method of claim 1, wherein the cells are human cells.

7. The method of claim 1, wherein the cells further express a recombinant polynucleotide encoding telomerase.

8. The method of claim 1, wherein the cells are βlox5 cells.

9. The method of claim 1, wherein the cells are a stable culture of endocrine β-cells.

10. The method of claim 1, wherein the pancreatic cell function comprises insulin production.

11. The method of claim 10, wherein the pancreatic cell function comprises glucose-responsive insulin production.

12. The method of claim 1, wherein the cells further express a recombinant oncogene.

13. The method of claim 12, wherein the cells express more than one recombinant oncogene.

* * * * *